United States Patent
Ito (10) Patent No.: US 9,289,166 B2
(45) Date of Patent: Mar. 22, 2016

(54) BIOLOGICAL INFORMATION MONITORING APPARATUS AND BIOLOGICAL INFORMATION MONITORING METHOD

(75) Inventor: Kazumasa Ito, Tokyo (JP)

(73) Assignee: NIHON KOHDEN CORPORATION, Tokyo (JP)

(*) Notice: Subject to any disclaimer, the term of this patent is extended or adjusted under 35 U.S.C. 154(b) by 430 days.

(21) Appl. No.: 13/444,205

(22) Filed: Apr. 11, 2012

(65) Prior Publication Data

US 2012/0265040 A1  Oct. 18, 2012

(30) Foreign Application Priority Data

Apr. 12, 2011  (JP) .................................. 2011-088571

(51) Int. Cl.
- *A61B 5/1455* (2006.01)
- *A61B 5/00* (2006.01)
- *G06F 19/00* (2011.01)

(52) U.S. Cl.
CPC .............. *A61B 5/1455* (2013.01); *A61B 5/7275* (2013.01); *G06F 19/345* (2013.01)

(58) Field of Classification Search
CPC ............... A61B 5/0002; A61B 5/1455; A61B 5/14551; A61B 5/14552; A61B 5/00; A61B 5/024; A61B 5/0245; A61B 5/145
USPC ......... 600/301, 310, 316, 322, 323, 324, 326, 600/473, 476, 508; 356/41
See application file for complete search history.

(56) References Cited

U.S. PATENT DOCUMENTS

| | | | | |
|---|---|---|---|---|
| 5,464,012 | A * | 11/1995 | Falcone | 600/301 |
| 6,223,064 | B1 * | 4/2001 | Lynn et al. | 600/324 |
| 6,754,516 | B2 * | 6/2004 | Mannheimer | 600/323 |
| 2004/0057037 | A1 | 3/2004 | Ohishi et al. | |
| 2005/0083193 | A1 * | 4/2005 | Al-Ali | 600/323 |
| 2008/0119705 | A1 | 5/2008 | Patel et al. | |
| 2010/0312176 | A1 | 12/2010 | Lauer et al. | |
| 2011/0054328 | A1 | 3/2011 | Hyogo et al. | |
| 2012/0116194 | A1 | 5/2012 | Gross et al. | |

FOREIGN PATENT DOCUMENTS

| | | |
|---|---|---|
| JP | 8-71046 A | 3/1996 |
| JP | 2001-70257 A | 3/2001 |
| JP | 2004-97781 A | 4/2004 |
| JP | 2007-117434 A | 5/2007 |
| JP | 2008-200111 A | 9/2008 |

(Continued)

OTHER PUBLICATIONS

Japanese Office Action for the related Japanese Patent Application No. 2011-088571 dated Dec. 13, 2013.

*Primary Examiner* — Eric Winakur
*Assistant Examiner* — Chu Chuan (JJ) Liu
(74) *Attorney, Agent, or Firm* — Kenealy Vaidya LLP (57) ABSTRACT

A biological information monitoring apparatus includes: an acquiring section configured to acquire biological information of a patient; a storage section configured to store a threshold which is changed with time from a first time; and a determining section configured to compare the biological information acquired by the acquiring section with a threshold corresponding to a second time when the biological information is acquired by the acquiring section, to perform determination of an abnormality of an living body of the patient.

13 Claims, 3 Drawing Sheets

(56) References Cited

FOREIGN PATENT DOCUMENTS

| | | |
|---|---|---|
| JP | 2010-510586 A | 4/2010 |
| JP | 2010-540133 A | 12/2010 |
| JP | 2011-50438 A | 3/2011 |
| JP | 2012-532728 A | 12/2012 |
| WO | 2011/007271 A1 | 1/2011 |

* cited by examiner

BIOLOGICAL INFORMATION MONITORING APPARATUS AND BIOLOGICAL INFORMATION MONITORING METHOD

This application claims the priority benefit under 35 U.S.C. §119 of Japanese Patent Application No. 2011-088571 filed on Apr. 12, 2011, which is hereby incorporated in its entirety by reference.

BACKGROUND OF THE INVENTION

The present invention relates to a biological information monitoring apparatus and a biological information monitoring method, and more particularly to a biological information monitoring apparatus and a biological information monitoring method in which an alarm threshold is adequately set.

In a clinical site, medical apparatuses for acquiring biological information related to sustention of the life and health of the patient are used in order to monitor the body condition of the patient. For example, the biological information includes the arterial oxygen saturation, the heart rate, the blood glucose level, the electroencephalogram, and the like, and is detected in the form of a biological signal by a sensor attached to the living body. In such medical apparatuses, there is an apparatus in which a threshold for a detected biological signal is set, and, when the biological signal reaches the threshold, it is determined that an abnormality occurs, and an alarm is activated. In response to the activating of the alarm, a medical person takes adequate measures, thereby enabling the life and health of the patient to be sustained.

As a technique related to the above, there is a medical apparatus in which current biological information is displayed and the threshold can be easily set on a touch panel (see JP-A-2001-070257).

In the technique disclosed in JP-A-2001-070257, the threshold can be set while monitoring the current biological information, but the threshold is allowed only to be set to a constant value. Even when the technique disclosed in JP-A-2001-070257 is applied to biological information which is changed with time in a normal state, therefore, there sometimes occurs a case where an abnormality cannot be detected. In the case where, with respect to biological information in which the measurement value is increased with time, the lower limit threshold is set based on an initial allowable range, after a biological signal once exceeds the threshold, the signal is always equal to or higher the lower limit threshold, and therefore the threshold is meaningless. By contrast, in the case where the lower limit threshold is set based on a final allowable range, the alarm is continued to activate until the signal reaches the threshold. In this case, even when the level of the biological signal is normally raised, it is determined to be abnormal. This causes a medical person to be unnecessarily worried, and surrounding persons to feel stress.

SUMMARY

It is therefore an object of the invention to provide a biological information monitoring apparatus which, also with respect to a biological signal that is changed with time, can adequately monitor an abnormality.

In order to achieve the object, according to the invention, there is provided a biological information monitoring apparatus comprising: an acquiring section configured to acquire biological information of a patient; a storage section configured to store a threshold which is changed with time from a first time; and a determining section configured to compare the biological information acquired by the acquiring section with a threshold corresponding to a second time when the biological information is acquired by the acquiring section, to perform determination of an abnormality of an living body of the patient.

The biological information monitoring apparatus may further comprise: a receiving section configured to receive an input of a plurality of sets each of which includes an arbitrary time and a threshold corresponding to the arbitrary time; and a setting section configured to set the threshold which is changed with time, based on the input plurality of sets.

The biological information monitoring apparatus may further comprise an alarm section, the determining section may determine whether the acquired biological information reaches the threshold, and the alarm section may be configured to issue an alarm when the determining section determines that the acquired biological information reaches the threshold.

The threshold stored in the storage section may include a plurality of thresholds which are changed with time, and each of the plurality of thresholds may correspond to a respective one of levels of the abnormality.

The storage section may further store a threshold which is not changed with time.

The first time may be one of a time when the determining section receives a user instruction, a time when the determining section performs determination based on a result of detection of other biological information provided by an external apparatus, and a time when staring to count time.

The biological information monitoring apparatus may further comprise a monitoring section configured to monitor a pattern of temporal change of the biological information, the storage section may store, in advance, a reference pattern of temporal change of the biological information, the determining section may collate the pattern monitored by the monitoring section with the reference pattern stored in the storage section, and the first time may be a time when the pattern monitored by the monitoring section is identical with the reference pattern stored in the storage section.

The biological information may include information related to an arterial oxygen saturation.

The alarm issued by the alarm section may include a plurality of different alarms, and each of the plurality of different alarms may correspond to a respective one of different levels of the abnormality.

The biological information monitoring apparatus may further comprise a display section on which the threshold which is changed with time and temporal change of the biological information which is acquired during the determination of the abnormality are displayed.

The threshold may be stepwisely changed with time.

The threshold may be changed stepwisely and sequentially based on a user input.

The threshold may be changed stepwisely and sequentially based on a user input.

The threshold may be stepwisely changed with time, and the alarm section may issue different alarms respectively for levels of the threshold which is stepwisely changed with time.

According to the invention, there is also provided a biological information monitoring method which is performed by a biological information monitoring apparatus configured to store a threshold which is changed with time from a first time, the biological information monitoring method comprising: acquiring biological information of a patient; and comparing the acquired biological information with a threshold corresponding to a second time when the biological information is acquired, thereby performing determination of an abnormality of a living body of the patient.

DETAILED DESCRIPTION OF EMBODIMENTS

First Embodiment

Hereinafter, embodiments of the invention will be described in detail with reference to the drawings.

Figure 1:
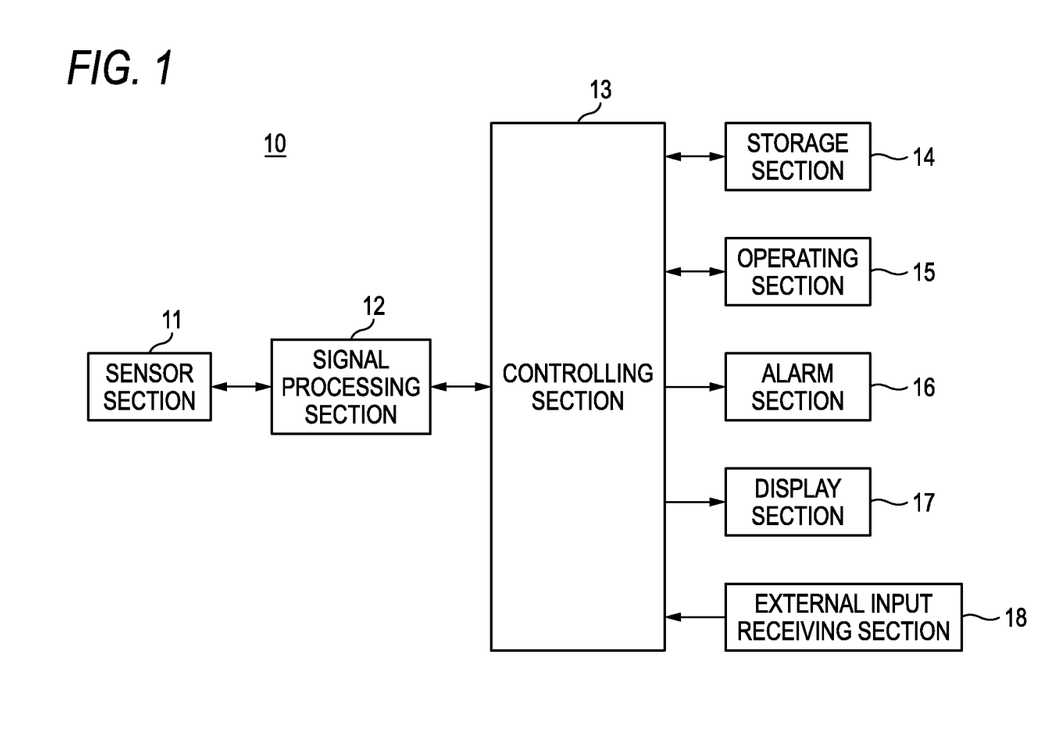
FIG. 1 is block diagram showing the entire configuration of a biological information monitoring apparatus of a first embodiment of the invention.

FIG. 1 is block diagram showing the configuration of a biological information monitoring apparatus of a first embodiment of the invention. The biological information monitoring apparatus 10 of the embodiment is configured as a bedside monitor, and has a sensor section 11, a signal processing section 12, a controlling section 13, a storage section 14, an operating section 15, an alarm section 16, a display section 17, and an external input receiving section 18. These components are connected to one another through, for example, a bus or cable for exchanging signals. The biological information monitoring apparatus 10 can invasively or non-invasively acquire biological information from the patient.

The sensor section 11 is attached to the living body of the patient to function as an acquiring section, thereby acquiring biological information from the living body. For example, the sensor section 11 is a probe, a cuff, or an electrode pad. The biological information acquired by the sensor section 11 is transmitted as, for example, an analog signal to the signal processing section 12.

The signal processing section 12 receives the biological information acquired by the sensor section 11, and processes the biological information. For example, the signal processing section 12 performs processes which are required depending on the kind of the biological information, such as signal amplification, FFT (Fast Fourier Transform), and A/D conversion, to convert the biological information to a biological signal which can be interpreted by the controlling section 13. The biological signal which is processed by the signal processing section 12 is transmitted to the controlling section 13. Depending on the kind of the biological information, the biological information may be transmitted to the controlling section 13 without being passed through the signal processing section 12, to be received by the controlling section.

The controlling section 13 is configured by a CPU (Central Processing Unit), a ROM (Read Only Memory) or a RAM (Random Access Memory), an interface, and the like. In accordance with programs, the CPU controls the above-described sections and executes various calculation processes. The ROM or the RAM stores various programs and data. The interface receives signals from the external input receiving section 18. These components are connected to one another by an internal bus of the controlling section 13. Each of the functions of the controlling section 13 is exerted by execution of a program corresponding to the function by the CPU.

The storage section 14 is configured by a flash memory, an HDD (Hard Disk Drive), or the like, and stores programs for controlling the components of the biological information monitoring apparatus 10 including the operating system, and also thresholds which are set for respective biological information, and the like. With respect to biological information which is changed with time in a specific biological condition such as a state where the living body is in an abnormal status, information of sets of a threshold and a time period is stored so that a threshold is changed with time. With respect to biological information which shows a predetermined temporal change pattern or a predetermined value, immediately before falling into a specific biological state (the biological information is not always identical with that which is changed with time in the specific biological state), furthermore, the storage section 14 stores in real time a temporal change pattern of the biological information measured by the sensor section 11 (hereinafter, it is assumed that the pattern contains the value itself of the biological information). With respect to necessary biological information, moreover, the storage section 14 stores settings of a plurality of different patterns and sound levels of alarms emitted from the alarm section 16. The storage section 14 may store also a history of alarms which were generated in the past time, and the like.

The operating section 15 receives a setting which is produced by the user including a medical person or the like, and which is related to a threshold. For example, the operating section 15 receives an input of a preset value of a set of a time period and a threshold, and transmits the input preset value to the storage section 14, so that the value is stored therein. The operating section 15 further receives a user instruction for starting monitoring of the pattern of the temporal change of the acquired biological information, and, in response to the instruction, the controlling section 13 starts the monitoring of biological information.

The alarm section 16 issues an alarm based on the determination by the controlling section 13. Specifically, in the case where the controlling section 13 determines that the biological information reaches the threshold, an instruction by the controlling section 13 for issuing an alarm is transmitted to the alarm section 16, and the alarm section 16 issues an alarm. The alarm section 16 may issue different alarms for the plurality of thresholds. Alternatively, the alarm section 16 may be configured so that, with respect to a threshold which is stepwisely changed with time, different alarms are issued for respective steps of the threshold. The alarms may be visually displayed on the display section 17.

The display section 17 is configured by an LCD (Liquid Crystal Display), an OLED (Organic Light Emitting Diode), or the like, and displays various information. Based on image data of the measurement value of biological information which are produced and transmitted by the controlling section 13, for example, the display section 17 displays the measurement value and the at least one threshold. For example, the measurement value and the threshold are displayed as a trend graph in the form of a line graph. The display section 17 may be configured as a touch panel which is integrated with the operating section 15.

The external input receiving section 18 receives a signal from an external apparatus. The external input receiving section 18 receives an input signal from an external apparatus, and transmits the input signal to the controlling section 13. In the controlling section 13, the input signal is collated with predetermined stored information. In the case where it is determined that coincidence is attained, determination of biological information by the controlling section 13 is started (the determination will be described later in detail). In the specification, for example, the external apparatus is a medical apparatus which acquires biological information that is different in kind from that acquired by the biological information monitoring apparatus 10.

The biological information monitoring apparatus 10 may include components other than those described above, or may not include a part of the above-described components.

Next, a process in which a threshold is set by the above-described components, it is determined whether the acquired biological information reaches the set threshold by comparing the threshold with the biological information, and an alarm is issued, will be described. The threshold is input by the user through the operating section 15 functioning as a reception section, and the input is transmitted to the controlling section 13 functioning as a setting section, and set therein. The set threshold is stored in the storage section 14. In response to the user input through the operating section 15 or the determination by a monitoring section which will be described later, the determination of an abnormality of biological information is started. In the process of determining an abnormality of biological information, biological information of the patient is acquired by the sensor section 11, and the acquired biological information is adequately processed by the signal processing section 12, and received by the controlling section 13. The controlling section 13 functions as a determining section to perform a process of comparing the received biological information with the threshold stored in the storage section 14, and determining whether the biological information reaches the threshold or not. If it is determined that the biological information reaches the threshold, the controlling section 13 instructs the alarm section 16 to issue an alarm. The alarm section 16 which receives the alarm instruction issues an alarm. As described later, the alarm level can be set to a plurality of steps, and the setting can be made for each threshold or each level of the threshold.

Next, the determination which is performed for starting the abnormality determination on the biological information by the monitoring section will be described. Also when it is not determined that biological information is abnormal, the controlling section 13 functions as the monitoring section to monitor a temporal change of the biological information which is received from the sensor section 11 through the signal processing section 12. A temporal change pattern of the biological information which is acquired during the monitoring process is stored in the storage section 14. The controlling section 13 collates the temporal change pattern of the biological information which is acquired during the monitoring, with a reference pattern (hereinafter, including a reference value corresponding to the value of the biological information) stored in the storage section 14, to determine whether they are coincident with each other or not. If it is determined that they are coincident with each other, the biological information monitoring apparatus 10 starts the process of determining an abnormality of the biological information. The reference pattern is a known pattern which shows a precursor of an abnormality of the living body with respect to the biological information detected by the biological information monitoring apparatus 10. In first aid, for example, brain hypothermia is sometimes performed for treating a brain disorder. In this case, when the body temperature which is lowered by the hypothermia treatment reaches a preset value (reference value), the target value of the brain pressure is switched to a lower value (for example, 10 mmHg) which is considered to be good as a result of a treatment, and then a process of determining an abnormality of the brain pressure is started. During the brain hypothermia, the hypothermia treatment is continued and necessary treatments are performed so that the brain pressure does not deviate from the management target value (threshold). When the brain pressure deviates from the management target value (threshold), this is informed by an alarm. When the necessary treatments are ended and it is detected that the body temperature is returned by a rewarm treatment, the target value of the brain pressure is automatically switched to a higher value (for example, 20 mmHg), and the determining process is continued until the brain pressure is stabilized. The reference pattern is not limited to biological information of the kind which is detected by the biological information monitoring apparatus 10. The external input receiving section 18 may receive biological information of different kinds, and collation may be performed on the different kinds of biological information with respect to reference patterns.

Hereinafter, a setting process in which, by the biological information monitoring apparatus of the embodiment, a threshold is set for issuing an alarm will be described in detail with reference to FIGS. 2 and 3.

Figure 2:
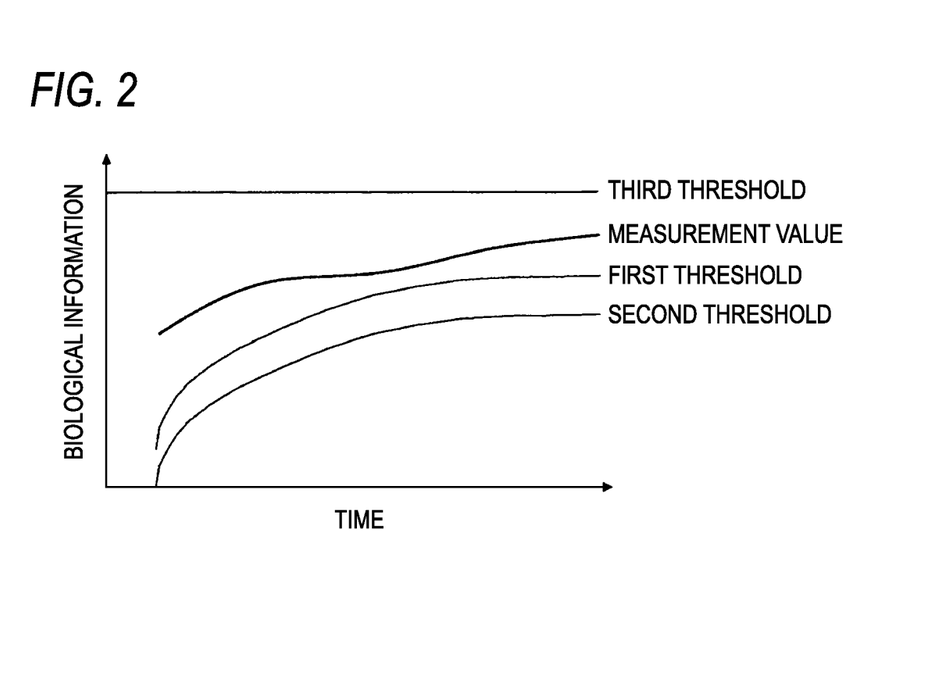
FIG. 2 is a view showing an example of a graph which schematically shows examples of thresholds set by the biological information monitoring apparatus shown in FIG. 1, and an acquired measurement value.
Figure 3:
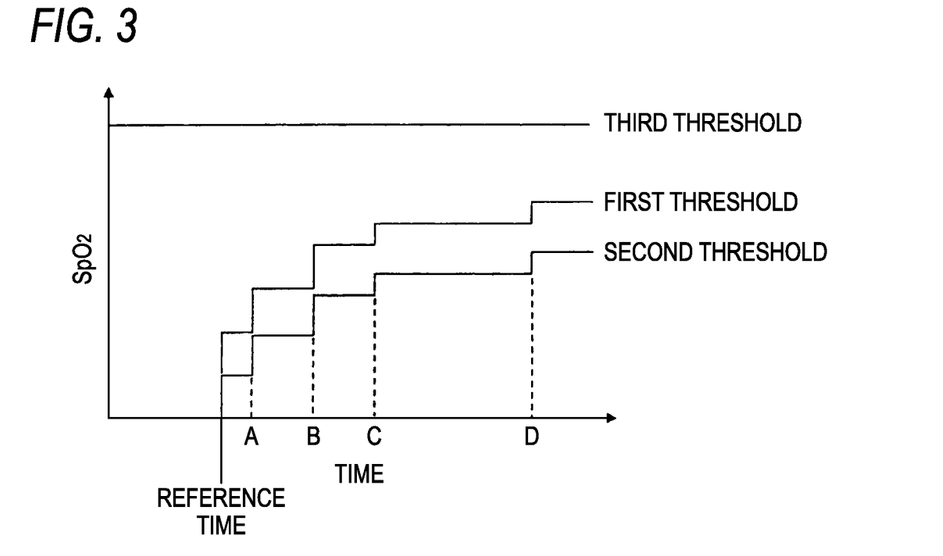
FIG. 3 is a view showing an example in which thresholds are switched at preset times in a graph of the thresholds in the first embodiment.

FIG. 2 is a view showing an example of a graph which schematically shows examples of thresholds set by the biological information monitoring apparatus shown in FIG. 1, and an obtained measurement value, and FIG. 3 is a view showing an example in which thresholds are switched at a preset time in a graph of the thresholds in the first embodiment.

As shown in FIG. 2, the time is set forth along the abscissa, and biological information is set forth along the ordinate. The measurement value of the biological information is temporally raised in a normal state. Therefore, first and second threshold are set so as to be raised with time with respect to the measurement value. As shown in FIG. 2, moreover, a third threshold may be set as a threshold which is not changed with time.

The thresholds and the measurement value are displayed so as to be comparable to one another. In FIG. 2, the measurement value is shown above the first threshold, and below the third threshold. Namely, the first threshold is set as the lower limit threshold of the measurement value, and the third threshold is set as the upper limit threshold. In order to set a threshold corresponding to an abnormal degree which is higher than the first threshold, the second threshold is set below the first threshold. In the embodiment, with respect to both the upper and lower limit thresholds, as described above, a threshold can be set for each of a plurality of levels of abnormality.

Next, a process will be described in detail in which a threshold is set with respect to the biological information that is shown in FIG. 2 and that is changed with time, and an abnormality is determined by determining whether the biological information reaches the threshold or not.

As shown in FIG. 3, as an example of biological information which is changed with time, there is the arterial oxygen saturation ($SpO_2$) of a neonatal infant immediately after birth. The $SpO_2$ is an important index which is used particularly when cardiopulmonary resuscitation is performed on a neonatal infant immediately after birth. During ten minutes after birth, an oxygen supply to a neonatal infant must be ensured so as to satisfy a predetermined $SpO_2$ value. In accordance with the body condition of a neonatal infant immediately after birth, for example, the measurement of $SpO_2$ is started at birth (reference time), 60% or more of $SpO_2$ must be ensured after one minute from the reference time, 70% or more must be ensured after three minutes, 80% or more must be ensured after five minutes, and 90% or more must be ensured after ten minutes. During this time period, the upper limit of the $SpO_2$ of the neonatal infant is maintained so as not to exceed 95%.

In the embodiment, with respect to such biological information, sets of a desired time period and a threshold can be set in order to set a threshold which is changed with time. As shown in FIG. 3, the temporal change of a threshold can be set so that the threshold is stepwisely changed with time. Table 1 below shows examples of such sets of a threshold and a time period for setting a threshold.

TABLE 1

Setting of alarm

| Elapsed time | First threshold | | Second threshold | | Third threshold | |
|---|---|---|---|---|---|---|
| | Threshold (%) | Alarm level | Threshold (%) | Alarm level | Threshold (%) | Alarm level |
| Start | 50 | Low | 40 | Medium | 95 | Medium |
| 1 min. | 60 | Low | 50 | Medium | | |
| 3 min. | 70 | Low | 60 | High | | |
| 5 min. | 75 | Low | 65 | High | | |
| 10 min. | 80 | Low | 70 | High | | |

FIG. 3 shows a manner in which thresholds are set with respect to a time period in accordance with the settings shown in Table 1. As shown in Table 1, sets of a time period and a threshold can be set for the first to third thresholds, respectively, and, in correspondence with the setting, the temporal change of the thresholds shown in FIG. 3 can be set. Specifically, "Reference time" in FIG. 3 corresponds to "Start" in Table 1, and "A" to "D" correspond to "1 min." to "10 min.", respectively. As the reference time, for example, the time when the temporal change pattern of the biological information monitored by the monitoring section is determined to be coincident with the reference pattern as described above, that when the controlling section 13 receives an instruction based on a user operation, or that when the determination of an abnormality of biological information is started can be set.

During the period of determining an abnormality of biological information by the biological information monitoring apparatus 10, in the case where the controlling section 13 determines that the measurement value of biological information reaches the first threshold, "Low" level alarm is issued from the alarm section 16 in accordance with the setting of the alarm level shown in Table 1. During the period from the start to three minutes, in the case where it is determined that the measurement value of biological information is lowered below the first threshold which is the lower limit, and reaches the second threshold which is the next lower limit, "Low" level alarm is switched to "Medium" level alarm in accordance with the alarm priority shown in Table 1. Namely, the determination that the measurement value reaches the second threshold means that a higher abnormality degree is determined. During the whole period, also when the measurement value reaches the third threshold which is the upper limit, "Medium" level alarm is issued. After elapse of three minutes from the start, in the case where the measurement value reaches the second threshold, the controlling section 13 determines that biological information reaches the second threshold, and "Low" level alarm is switched to "High" level alarm.

According to the embodiment, as described above, sets of a time period and a threshold are set, whereby a threshold which is changed with time can be set, and an adequate threshold conforming to biological information which is changed with time can be set. Even when biological information is changed with time, therefore, a situation where a threshold for the biological information becomes meaningless, or an alarm against the target value of the final threshold is continued to be issued can be prevented from occurring.

Therefore, a more appropriate treatment can be applied to the patient, and a more comfortable medical environment can be established.

Second Embodiment

Next, a second embodiment of the invention will be described in detail with reference to FIG. 4. Description of the configuration of the biological information monitoring apparatus 10, and the other configuration identical with configuration of the first embodiment is omitted in order to avoid duplication.

Figure 4:
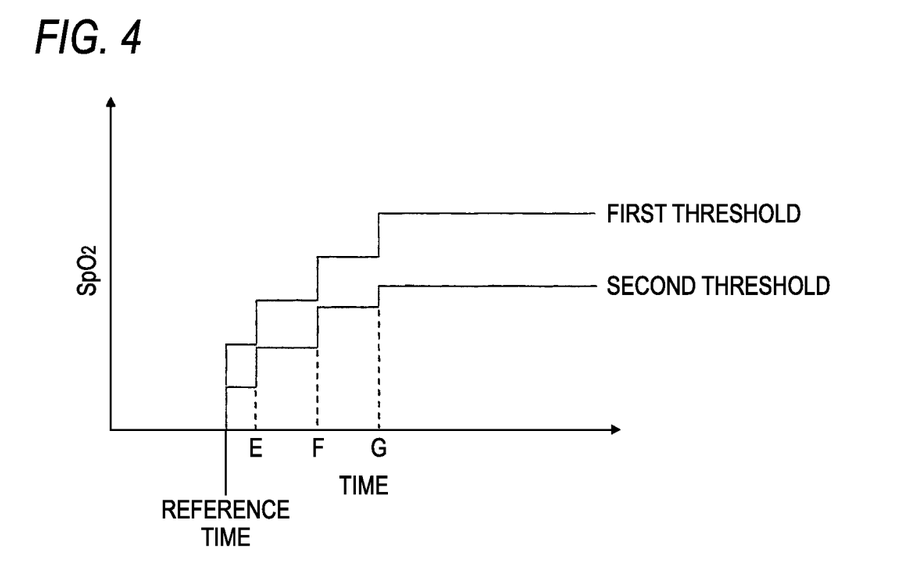
FIG. 4 is a view showing an example in which thresholds are manually switched in a graph of the thresholds in a second embodiment.

FIG. 4 is a view showing an example in which thresholds are manually switched in a graph of the thresholds in the embodiment. In the embodiment, in the case where a threshold is set so as to be stepwisely changed with time, the timing of changing the threshold can be manually operated. As shown in Table 2 below, for example, the level of the threshold can be changed by a user operation irrespective of the elapsed time from the start.

TABLE 2

Setting of alarm

| Switching | First threshold | | Second threshold | |
|---|---|---|---|---|
| | Threshold (%) | Alarm level | Threshold (%) | Alarm level |
| Start | 50 | Low | 40 | Medium |
| Operation 1 | 60 | Low | 50 | Medium |
| Operation 2 | 70 | Low | 60 | High |
| Operation 3 | 80 | Low | 65 | High |

FIG. 4 shows a manner in which thresholds are changed in accordance with the settings shown in Table 2. As shown in Table 2, sets of a time period and a threshold is set for the first and second thresholds, respectively, and, in correspondence with the setting, the temporal change of each of the thresholds shown in FIG. 4 is set. Specifically, "Reference time" in FIG. 4 corresponds to "Start" in Table 2, and "E" to "G" correspond to "Operation 1" to "Operation 3", respectively. The alarm levels with respect to the first and second thresholds shown in Table 2 are set as described with reference to Table 1 above. The operation of switching the threshold to the next step can be achieved by reception of a user input by the operating section 15.

According to the embodiment, in addition to the effects of the first embodiment, as described above, the user can advance flexibly and sequentially the level of the threshold in accordance with the progress status of the treatment in a clinical site. Therefore, a more appropriate treatment can be performed.

The invention is not limited to the above-described embodiments, but can be variously modified within the scope of the claims.

The first embodiment in which the threshold is stepwisely changed with time may be combined with the second embodiment in which the threshold is manually switched over. In the case where the threshold is manually switched over, the time when the threshold is switched to the next level may correspond to an elapsed time period which is continuous from the start, or may be a timing when a preset time period, which is previously set for the threshold, has elapsed. The time period when the threshold is stepwisely changed may be a standard one, or the maximum allowable one. According to the configuration, the effects of the first and second embodiments are attained, and further flexibility is provided to the user, so that a more appropriate treatment can be performed.

In the above, the embodiments in which the threshold is stepwisely changed have been described by using the specific example. However, the invention is not limited to the embodiments. Also a threshold which is not stepwisely changed, but gradually changed with time can be set. With respect to sets of a time period and a threshold shown in Table 1, for example, the threshold in each time period of the sets may not be constant but may be set so that the threshold is changed in a linear or quadratic function-like manner. According to the configuration, a threshold which is continuously changed with time can be set. In this case, different alarm levels may be set for predetermined threshold widths, respectively.

In the embodiments, the $SpO_2$ has been described as the biological information which is changed with time. However, the biological information is not limited to this. Another example of biological information to which the invention can be applied is bilirubin. During a light treatment, bilirubin in the body of a neonatal infant is changed with time. When the invention is applied, therefore, a more appropriate treatment can be performed.

In the embodiments, the configurations where sets of a time period and a threshold are provided in the form of a lookup table as shown in Tables 1 and 2 have been described. However, the invention is not limited to this. Any kind of format may be used.

The setting of the alarm level may be based on a user input through the operating section 15, or an input from an external apparatus (not shown) through the external input receiving section 18. For example, a configuration may be employed where a PC (Personal Computer) on which an application dedicated for the setting is installed is connected through the external input receiving section 18, and the setting can be performed by the PC. The alarm level can be set by the controlling section 13 based on the input.

Although, in the embodiments, a bedside monitor has been exemplified as the biological information monitoring apparatus, the invention is not limited to this. The invention may be applied to a central monitoring system in which a wireless or wired network is used.

According to an aspect of the invention, the threshold is set so as to be changed with time, and hence an adequate threshold according to a monitor object can be set also with respect to a biological signal that is changed with time. Therefore, a more appropriate treatment can be applied to the patient, and a more comfortable medical environment can be established.

What is claimed is:

1. A biological information monitoring apparatus comprising:
    an acquiring section configured to acquire biological information of a patient;
    a storage section configured to store a threshold which is changed with time, the threshold being set to correspond to an elapsed time from a reference time;
    a determining section configured to perform determination of an abnormality of a living body of the patient by comparing the biological information acquired by the acquiring section with the threshold corresponding to a time point when the biological information is acquired by the acquiring section;
    a monitoring section configured to monitor a pattern of temporal change of the biological information, wherein:
    the storage section stores, in advance, a reference pattern of temporal change of the biological information;
    the determining section collates the pattern monitored by the monitoring section with the reference pattern stored in the storage section;
    the determining section determines, as the reference time, a time when the pattern monitored by the monitoring section is identical with the reference pattern stored in the storage section; and
    the determining section starts a process of performing the determination of the abnormality of the living body of the patient at the reference time.

2. The biological information monitoring apparatus according to claim 1, further comprising:
    a receiving section configured to receive an input of a plurality of sets each of which includes an arbitrary time and a threshold corresponding to the arbitrary time; and
    a setting section configured to set the threshold which is changed with time, based on the input plurality of sets.

3. The biological information monitoring apparatus according to claim 1, further comprising an alarm section, wherein:
    the determining section determines whether the acquired biological information reaches the threshold; and
    the alarm section is configured to issue an alarm when the determining section determines that the acquired biological information reaches the threshold.

4. The biological information monitoring apparatus according to claim 1, wherein:
    the threshold stored in the storage section includes a plurality of thresholds which are changed with time; and
    each of the plurality of thresholds corresponds to a respective one of levels of the abnormality.

5. The biological information monitoring apparatus according to claim 1, wherein the storage section further stores a threshold which is not changed with time.

6. The biological information monitoring apparatus according to claim 1, wherein the biological information includes information related to an arterial oxygen saturation.

7. The biological information monitoring apparatus according to claim 3, wherein:
    the alarm issued by the alarm section includes a plurality of different alarms; and
    each of the plurality of different alarms corresponds to a respective one of different levels of the abnormality.

8. The biological information monitoring apparatus according to claim 1, further comprising a display section on which the threshold which is changed with time and temporal change of the biological information which is acquired during the determination of the abnormality are displayed.

9. The biological information monitoring apparatus according to claim 1, wherein the threshold is stepwisely changed with time.

10. The biological information monitoring apparatus according to claim 9, wherein the threshold is changed stepwisely and sequentially based on a user input.

11. The biological information monitoring apparatus according to claim 1, wherein the threshold is changed stepwisely and sequentially based on a user input.

12. The biological information monitoring apparatus according to claim 3, wherein:
    the threshold is stepwisely changed with time; and
    the alarm section issues different alarms respectively for levels of the threshold which is stepwisely changed with time.

13. A biological information monitoring method which is performed by a biological information monitoring apparatus configured to store a threshold which is changed with time, and a reference pattern of temporal change of biological information, in advance, the threshold being set to correspond to an elapsed time from a reference time, the biological information monitoring method comprising:
- acquiring the biological information of a patient;
- comparing the acquired biological information with a threshold corresponding to a time point when the biological information is acquired, thereby performing determination of an abnormality of a living body of the patient;
- monitoring a pattern of temporal change of the biological information;
- collating the monitored pattern with the stored reference pattern;
- determine, as the reference time, a time when the monitored pattern is identical with the stored reference pattern stored; and
- starting a process of performing the determination of the abnormality of the living body of the patient at the reference time.

* * * * *